United States Patent
Menon et al.

(10) Patent No.: US 6,447,815 B1
(45) Date of Patent: Sep. 10, 2002

(54) HEATED ALCOHOL EXTRACTION OF HERBS

(75) Inventors: Gopi R. Menon, Riverside; Ernesto A. Brovelli, Corona; Luis I. Vergel de Dios, Walnut, all of CA (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 09/741,551

(22) Filed: Dec. 19, 2000

(51) Int. Cl.⁷ ................................................ A61K 35/78
(52) U.S. Cl. ...................... 424/737; 424/725; 424/451; 424/456; 424/464
(58) Field of Search ................................ 424/725, 737, 424/451, 456, 464

(56) References Cited

U.S. PATENT DOCUMENTS

| | | |
|---|---|---|
| 3,862,317 A | 1/1975 | Lal Anand |
| 5,061,403 A | 10/1991 | Todd, Jr. |
| 5,064,675 A | 11/1991 | Jensen et al. |
| 5,093,122 A | 3/1992 | Kodera |
| 5,176,913 A | 1/1993 | Honerlagen et al. |
| 5,578,307 A * | 11/1996 | Wunderlich et al. ..... 424/195.1 |
| 5,603,935 A | 2/1997 | Jian et al. |
| 5,660,832 A | 8/1997 | Steiner et al. |
| 5,876,728 A | 3/1999 | Kass et al. |
| 5,919,511 A | 7/1999 | Hagiwara |

FOREIGN PATENT DOCUMENTS

| | | |
|---|---|---|
| CA | 2019718 | 12/1991 |
| DE | 37 44570 A1 | 7/1989 |
| EP | 0464298 B1 | 6/1995 |
| GB | 2327607 A * | 2/1999 |
| RO | 96961 A | 5/1989 |
| WO | WO 99/20289 | 4/1999 |

OTHER PUBLICATIONS

Bergeron et al.,Phytochemical Analysis, 2000, 11:207–215.*

* cited by examiner

*Primary Examiner*—Christopher R. Tate
*Assistant Examiner*—Kailash C. Srivastava
(74) *Attorney, Agent, or Firm*—Warner Norcross & Judd LLP

(57) ABSTRACT

The present invention relates to methods for the extraction of herbs and plant materials. More particularly, the present invention relates to extraction methods for Echinacea. The extraction methods of the present invention provide a higher soluble solids content and a higher level of desired marker compounds, such as alkylamides, than conventional extraction procedures. Thus, the extraction methods of the present invention result in a greater yield at a lower cost from a given amount of starting material.

20 Claims, 7 Drawing Sheets

HERB EXTRACTION FLOWCHART

HERB EXTRACTION FLOWCHART

ECHINACEA EXTRACTION FLOWCHART

HEATED ALCOHOL EXTRACTION OF HERBS

BACKGROUND OF THE INVENTION

The present invention relates to novel methods for the extraction of herbs and plant materials. More particularly, the present invention relates to extraction methods for Echinacea. The extraction methods of the present invention provide a higher soluble solids content and a higher level of desired marker compounds, such as alkylamides, than conventional extraction procedures. Thus, the extraction methods of the present invention result in a greater yield at a lower cost from a given amount of starting material.

Typical processes for the extraction of nutrients from herbs use water or alcohol. In traditional processes, however, ambient temperature water or alcohol is generally used for the extraction. Typical processes involve taking the herb, milling it, and extracting the herb with alcohol and water at some strength of alcohol, generally 70% to 90%, for a few hours to extract soluble solids and nutrients.

Echinacea contains numerous active phytochemicals that have immunomodulatory and other beneficial activities. There is a long tradition of the use of Echinacea preparations in the adjuvant therapy of inflammations, skin damage, and, more typically, infections. The Echinacea plant is a popular herbal immunostimulant. The ability of Echinacea to stimulate the immune system in a nonspecific manner is exemplified in the enhancement of phagocytosis seen in cells treated with Echinacea (see, Sun et al., The American coneflower: a prophylactic role involving nonspecific immunity, *J. Altern. Complement Med.*, 5(5): 437–446 (1999)). Echinacea's immunomodulatory activity has been attributed to various actives, including alkylamides, phenolics, polysaccharides, alkaloids, glycoproteins, and flavonoids (see, Bauer, R. and Wagner, H., Echinacea species as potential immunostimulatory drugs, in *Economic and Medicinal Plant Research*, Ch. 8, p.253, Wagner, H. and Farnsworth, N. R. (Editors), Academic Press Limited, New York, N.Y., (1991)).

It is, therefore, desirable to develop more efficient and cost-effective methods of extracting nutrients from herbs such as Echinacea.

SUMMARY

The present invention relates to novel methods for the extraction of herbs and plant materials. The extraction methods of the present invention result in greater yields at lower cost than conventional extraction processes.

In one aspect, the present invention relates to extraction methods that result in higher yields of soluble solids than conventional extraction processes.

In another aspect, the present invention relates to extraction methods that result in higher levels of marker compounds, such as alkylamides, than conventional extraction processes.

In another aspect, the present invention relates to extraction methods that yield material with better tableting characteristics than conventional extraction processes.

In another aspect, the present invention relates to extraction methods that are lower in cost than conventional extraction processes. The methods of the present invention result in better quality yields and higher yields from a given amount of starting material, thereby decreasing the cost of the final product.

DETAILED DESCRIPTION OF THE INVENTION

In accordance with the present invention, novel methods for the extraction of herbs and plant materials are provided. The extraction methods of the present invention provide greater yields at lower costs than conventional extraction processes. The novel extraction methods of the present invention yield a product with higher yields of soluble solids, higher levels of marker compounds, such as alkylamides, and better tableting characteristics than conventional extraction processes.

Although the experiments described herein use *Echinacea angustifolia* and *Echinacea purpurea*, the contemplated scope of present invention is not limited to these two species, or to Echinacea species in general, but includes all species of herbs or plant materials. Presently preferred, however, are *Echinacea anglustifolia* and *Echinacea purpurea* which are used in the experiments described herein.

Experiments were carried out to determine optimal extraction conditions to yield maximum soluble solids. Maximizing soluble solids is important to keep the cost of extraction low while maintaining a high yield of dry extract.

Figure 1:
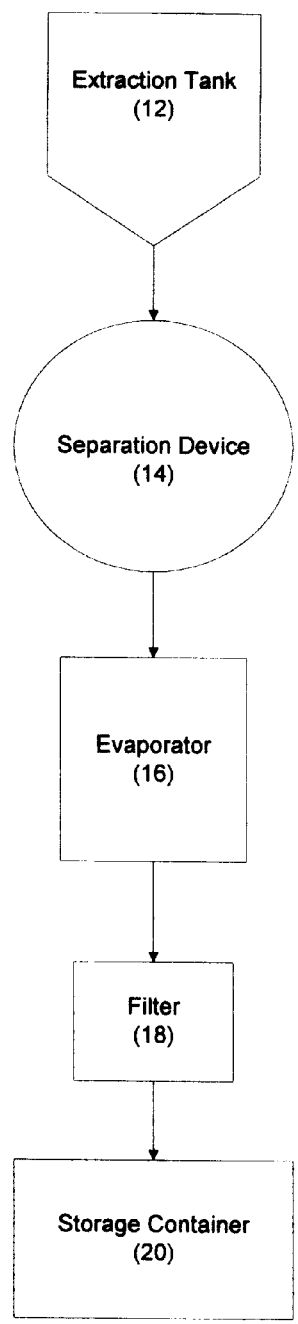
FIG. 1 is a flow chart illustrating an herb extraction process according to the present invention.

The extraction process is generally illustrated in FIG. 1. The extraction process can be used for any type of herb or plant material. Before starting the batch, all equipment used for processing is cleaned and sanitized. A sample of starting material (the dried herb root) is collected for analysis. The raw starting material is weighed and added to the extraction tank (12). An alcohol solution is fed into the extraction tank (12). The extraction tank (12) is heated and the contents of the tank are preferably agitated during the extraction. The extraction is carried out for about two hours, maintaining temperature and agitation throughout. The percentage of soluble solids present is monitored during the extraction, for example, by measuring the refractive index.

After the extraction, the contents of the extraction tank are preferably cooled to ambient temperature by circulating cool water through the jacket of the extraction tank. The non-soluble solids are then separated from the liquid extract with a separation device (14). Separation can be carried out, for example, using a filtration device, a centrifuge, a screw press, or any other separation device. At this point, a sample of liquid extract may be collected for analysis of desired marker compounds.

The liquid extract is loaded into an evaporator (16), and the temperature is raised in order to distill off the alcohol. Distillation is complete when the alcohol stops boiling off.

This can be confirmed by measuring the percent of soluble solids in the concentrate. The target for soluble solids is about 9–11% after distillation is complete.

The liquid extract is then concentrated by evaporation to a target level of soluble solids and transferred to covered containers. The target level of soluble solids depends on the end use of the product. The liquid extract is generally concentrated to a target level from about 2 to 3% soluble solids to about 20 to 45% soluble solids in the concentrate for applications where one spay dries, freeze dries, tray dries, or vacuum dries the concentrate to produce a powdered extract. The powdered extract can then be used as granules or used "as is" to make tablets, two-piece hard shell capsules, or other forms. The liquid extract can also be concentrated from about 2 to 3% soluble solids to about 20 to 30% soluble solids and alcohol (grain or organic) can be added to make a spray-type product or a dropper-type product.

Using Echinacea, a series of experiments were conducted to determine the optimal conditions for the extraction process. Alcohol concentrations between 50% and 90% alcohol were tested. An alcohol concentration of about 70% was found to be optimal. Lower alcohol concentrations yield a lower levels of soluble solids. Higher alcohol concentrations of about 85% to 90% can yield a higher level of alkylamides, but the yield of other important phytochemicals, such as polysaccharides are reduced. Additionally, using the higher alcohol concentrations greatly increases the cost of the extraction process and may therefore be cost prohibitive.

Various extraction temperatures ranging from ambient temperature (approximately 18° C. to 24° C.) to about 70° C. were tested. The yield of soluble solids from the extraction generally increases with increasing extraction temperature. As the extraction temperature reaches about 65° C. to 70° C., nearing the boiling point of alcohol, there are increased emissions from the heated alcohol. The extraction temperature of about 60° C. was found to be optimal.

The extraction time was also tested. As seen in Table 1 and Table 2, the yield of soluble solids generally peaks at about 105–120 minutes of extraction. Many experiments were carried out with longer extraction times, but extraction times of up to about 6.3 hours have a shown similar mass of soluble solids and similar alkylamides yields as the 2-hour extraction. Longer extraction times yield diminishing returns and significantly increase the cost of the extraction, as found in experiments conducted with extraction times up to about six hours. Therefore, an extraction time of about 2 hours is considered optimal.

Figure 2:
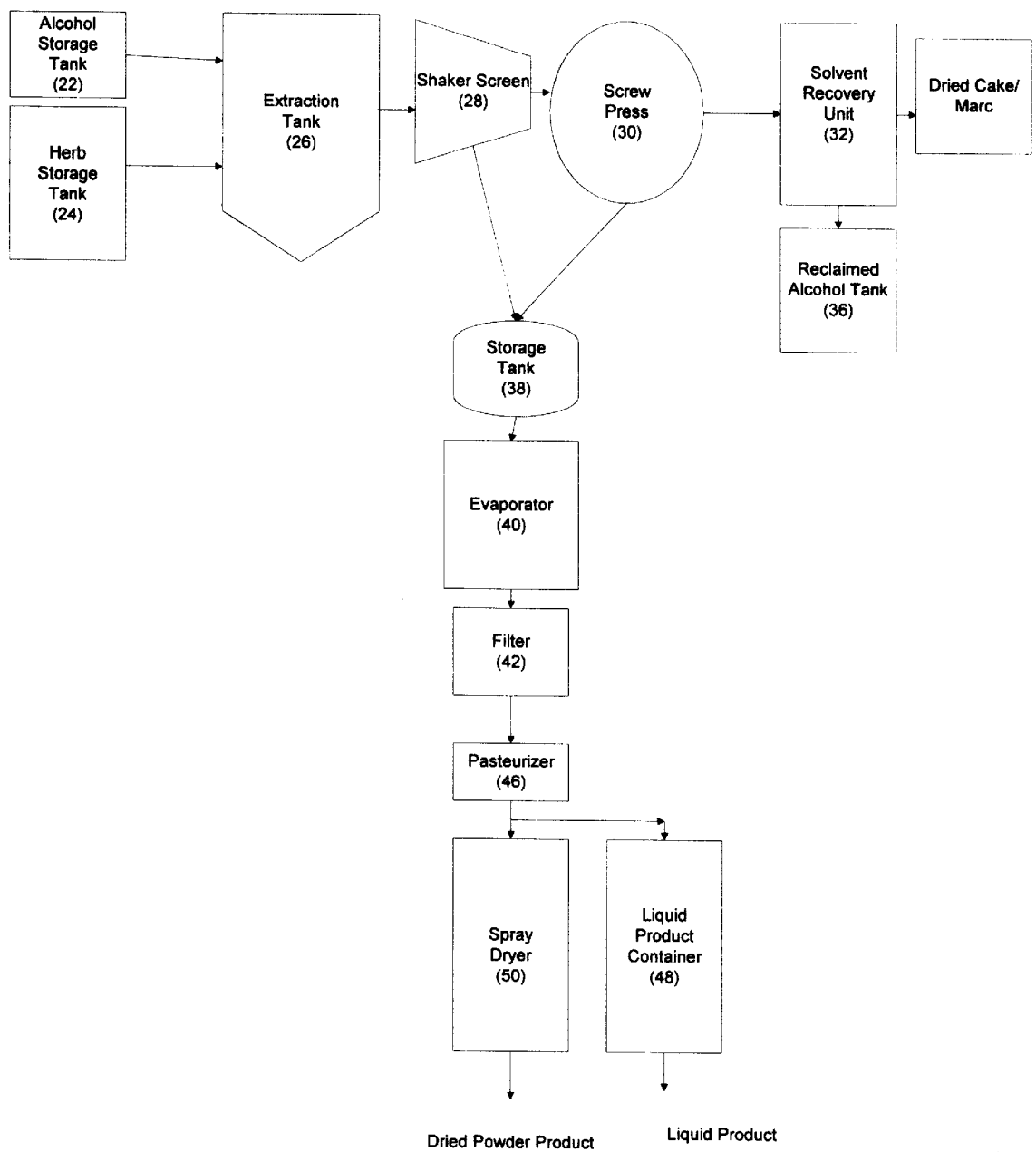
FIG. 2 is a flow chart illustrating a preferred embodiment of an herb extraction process according to the present invention.
Figure 3:
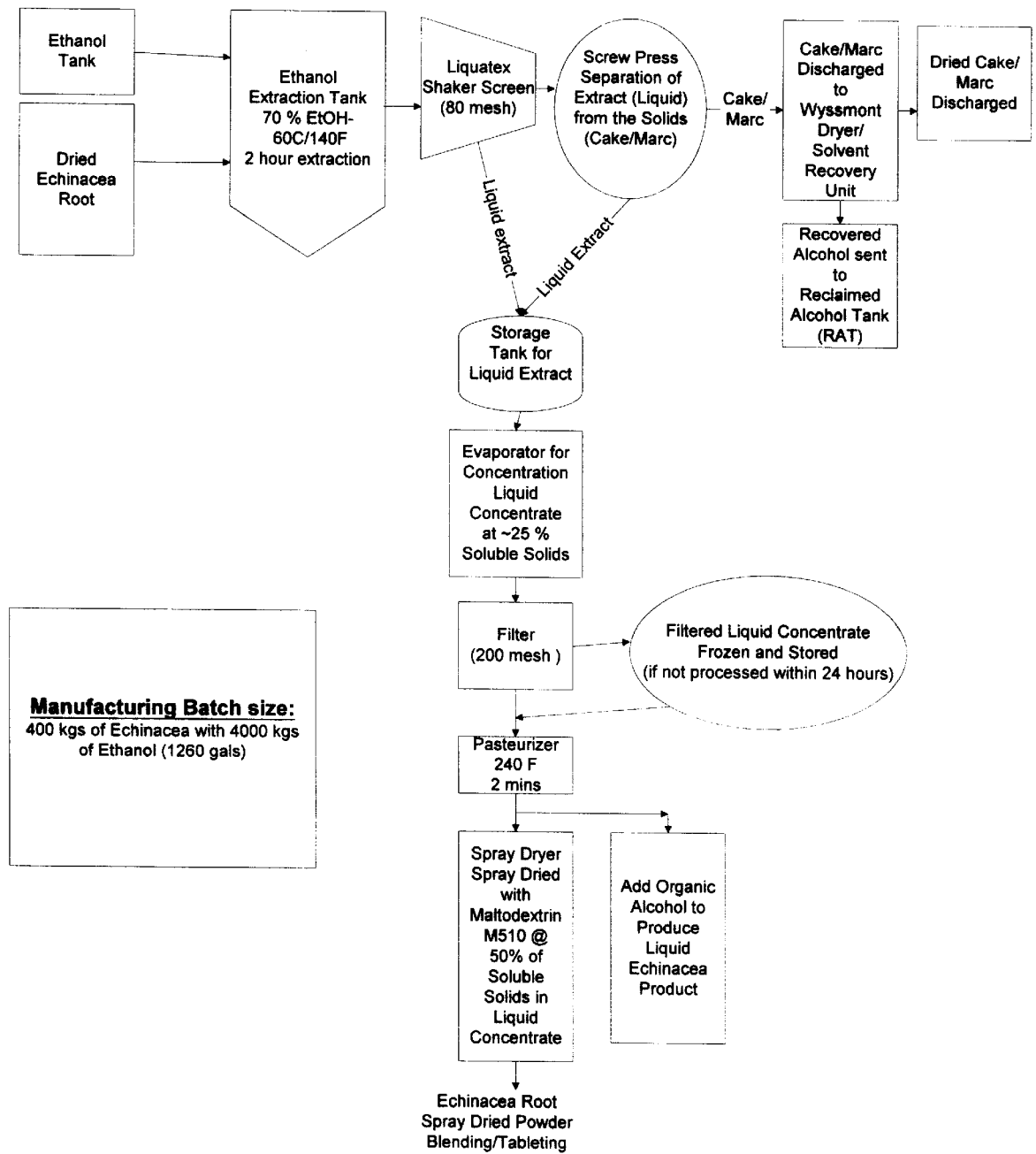
FIG. 3 is a flow chart illustrating one preferred embodiment of an Echinacea root extraction processing according to the present invention.

A preferred embodiment of the extraction process for Echinacea is illustrated in FIG. 2 and FIG. 3. A manufacturing batch size would contain, for example, 400 Kg Echinacea and 4000 Kg ethanol (1260 gallons). Before starting the batch, all equipment used for processing is cleaned and sanitized. One (1) Kg of starting material is collected for analysis. The starting material is stored in an herb storage tank (24). The raw starting material is weighed and added to the extraction tank (26). An ethanol/water mixture is made of about 70% ethanol and 30% water in a quantity sufficient to give a 1:10 ratio (weight: weight) of raw herb material to solvent. The ethanol/water mixture is stored in an alcohol storage tank (22). The alcohol is then fed into the extraction tank (26). The extraction tank (26) is heated to 60° C./140° F., and the contents of the extraction tank (26) are agitated during the extraction. The extraction is carried out for about two hours after reaching 60° C./140° F., maintaining temperature and agitation throughout. The percentage of soluble solids present is monitored during the extraction. Soluble solids can be measured, for example, by measuring the refractive index of the extract with a refractometer or through a loss on drying (LOD) technique.

After the extraction is complete, the contents of the tank are preferably cooled to ambient temperature by circulating cool water in the jacket of the extraction vessel. The slurry from the tank is then pumped out to separate the non-soluble solids from the liquid extract using a separation device (14). Separation can be carried out, for example, using a filtration device, a centrifuge, a screw press, or any other separation device. In one preferred embodiment, a shaker screen (28) and a screw press (30) are used to separate the liquid extract from the solids (referred to as cake or marc). At this point, a 100 ml sample of liquid extract may be collected for analysis of alkylamides.

The liquid extract from both the shaker screen (28) and the screw press (30) are transferred to a storage tank (38). From the storage tank (38), the liquid extract is loaded into an evaporator (40), and the temperature is brought to about 77° C.(170° F.), to distill off the alcohol. Distillation is complete when the alcohol stops boiling off. This can be confirmed by measuring the percent of soluble solids in the concentrate. The target for soluble solids is about 9–11% after distillation is complete. A 100 ml sample of the liquid concentrate is collected for analysis of alkylamides.

The liquid extract is then concentrated through evaporation. The evaporation is carried out in an evaporator (40) to a target of about 25%±2% soluble solids. The level of soluble solids is monitored using a refractometer every 30 minutes until the target is achieved. Depending on the desired end product, the liquid extract is then optionally filtered through a filter (42) to remove remaining insoluble solids. For example, if the end product is a liquid (for dropper or spray-type product), it is desirable to filter off any insoluble solids. For a liquid product, the extract is preferably filtered through a filter with a minimum of at least about a 200 mesh. This removes particulate matter that could otherwise interfere with the delivery of the liquid product by, for example, clogging a spray bottle. Alternatively, if the end product is a solid powder, it is not necessary to remove remaining insoluble solids.

At this point, the concentrated liquid extract is frozen and stored if it is not to be further processed with 24 hours. As processing continues, the concentrated liquid extract is then pasteurized in a pasteurizer (46) at 240° F. for two minutes to kill any bacteria that may be present in the extract. From the pasteurizer (46), the extract is further processed for a liquid end product or a powder end product. For a liquid end product, the extract is transferred to a liquid product container (48) and organic alcohol is added to produce a liquid Echinacea product.

Alternatively, if a dry product is desired, the extract is transferred to a spray dryer (50). Maltodextrin is added in an amount equal to 50% of the mass of the soluble solids present in the liquid concentrate, and the product is spray dried. The spray-dried powder can then be blended with other ingredients and/or formed into tablets for the final product.

In one preferred embodiment, the extraction process includes a solvent recovery system. After the initial extraction, the non-soluble solids are separated from the liquid extract using a separation device (14, FIG. 1) (28 and 30, FIG. 2). After separation, the non-soluble solids are transferred to a solvent recovery unit (32) in which the alcohol solvent is dried off of the non-soluble solids. The non-soluble solids are separated and discharged appropriately. The recovered solvent is stored in a reclaimed alcohol tank (36). The recovered alcohol can then be reused in subsequent extractions. The solvent recovery system increases the efficiency and reduces the cost of extraction. It is possible to recover up to 95% of the alcohol used in the extraction. Additionally, by removing the alcohol from the dried cake or marc (the non-soluble solids), the solids can be more easily disposed of.

In another series of experiments, four alcohol extraction processes were carried out using the roots of each of two Echinacea species: *Echinacea purpurea* and *Echinacea angustifolia*. The raw material was Trout Lake Farm tea-cut in all cases. The two variables for each root extraction process were (1) the alcohol to root ratio (by weight), and (2) the temperature at which the extraction was carried out. The two alcohol to root ratios used were (a) 10:1 and (b) 7:1. The two temperatures used were (a) unheated, or ambient temperature (approximately 65° F. to 75° F. or 18° C. to 24° C.) and (b) heated, or approximately 60° C./140° F. For each extraction, the process included extraction, concentration, and spray drying.

Unexpected and surprising results were found with the extraction using heated alcohol at a 10:1 alcohol to root ratio in the case of both *Echinacea purpurea* and *Echinacea angustifolia* roots. The heated extractions using a 10:1 alcohol to root ratio generally produced 40% to 50% more soluble solids, concentrated well, and spray dried (with M510-Maltodextrin) at a higher efficiency to produce a better spray dried powder (one that was non-sticking and had lower moisture uptake) compared to the unheated extractions.

Figure 4:
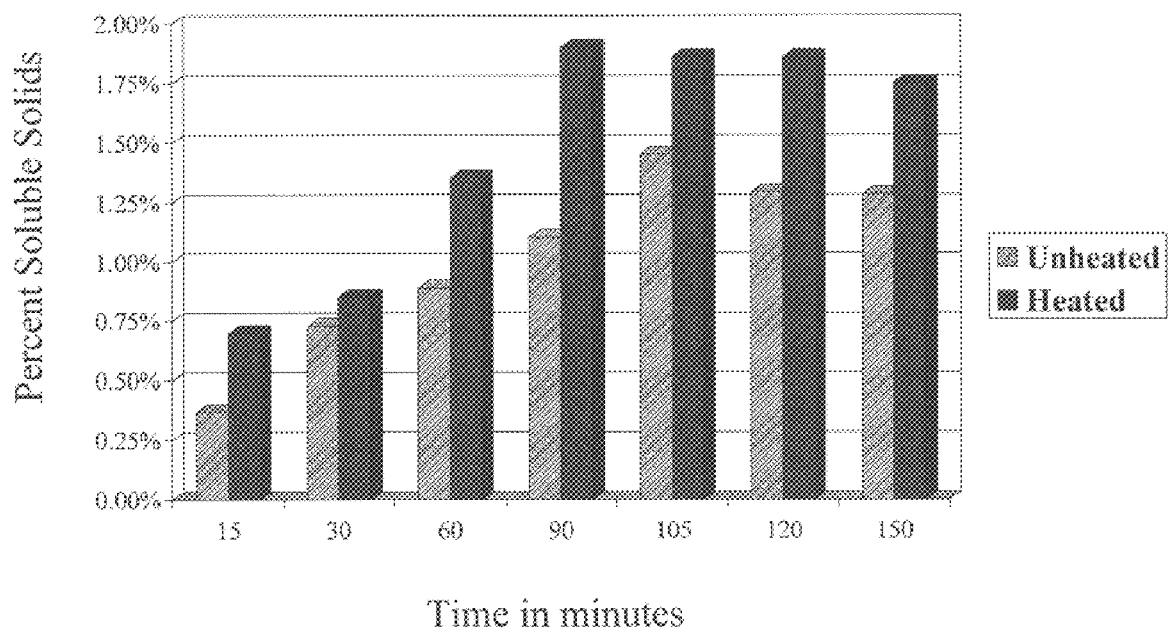
FIG. 4 is a graph illustrating the percent of soluble solids from heated and unheated *Echinacea purpurea* extractions using a 10:1 alcohol to root ratio.
Figure 5:
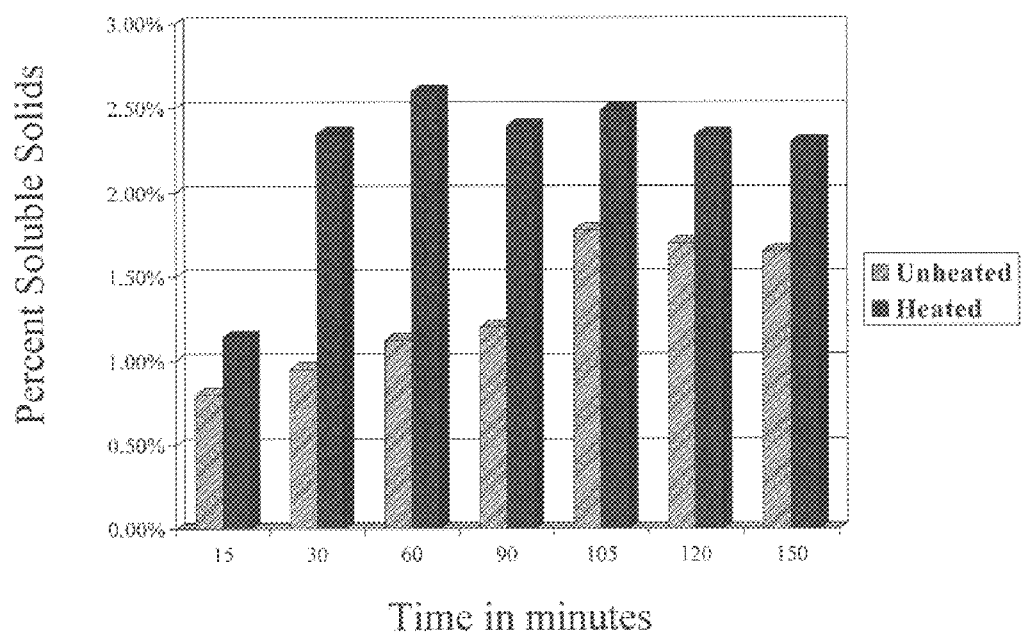
FIG. 5 is a graph illustrating the percent of soluble solids from heated and unheated *Echinacea angustifolia* extractions using a 10:1 alcohol to root ratio.

Table 1 and FIG. 4 show the percent of soluble solids present in both heated and unheated *Echinacea purpurea* extractions using a 10:1 alcohol to root ratio. Table 2 and FIG. 5 show the percent of soluble solids present in both heated and unheated *Echinacea angustifolia* extractions using a 10:1 alcohol to root ratio. The heated extractions yield higher levels of soluble solids throughout the course of the extraction.

Powder characteristics were compared for each of the four extract samples (*Echinacea purpurea*, heated and unheated, and *Echinacea angustifolia*, heated and unheated). All of the samples have "no flow." No flow is a measure of the stickiness or flowability of a material, and can be measured by the rate at which a material flows through a cone or funnel. For tableting, no flow is a characteristic that is not preferred. The samples with the best powder characteristics, however, were the powders made with the heated alcohol extraction process.

Figure 6:
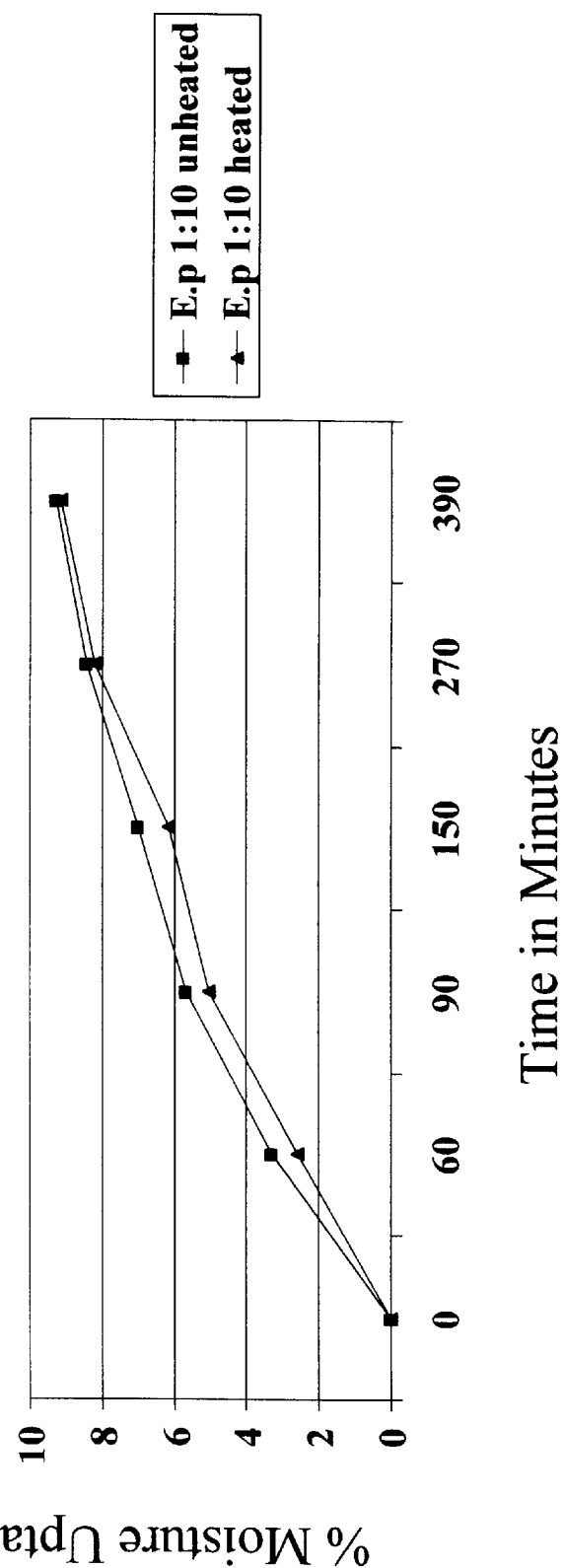
FIG. 6 is a graph illustrating moisture uptake of *Echinacea purpurea* extractions using a 10:1 alcohol to root ratio.
Figure 7:
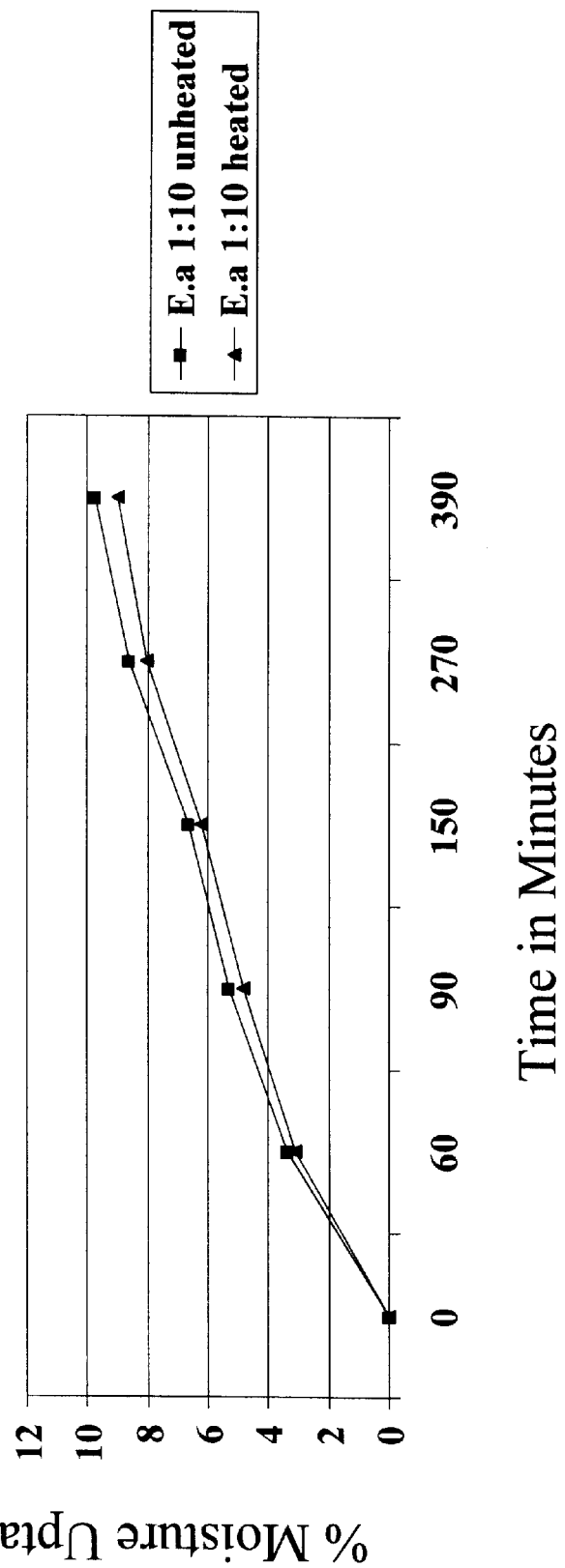
FIG. 7 is a graph illustrating moisture uptake of *Echinacea angustifolia* extractions using a 10:1 alcohol to root ratio.

Table 3 shows the results for moisture uptake for spray-dried extracts of *Echinacea purpurea* and *Echinacea angustifolia* prepared by both the heated and unheated extraction methods. FIG. 6 illustrates the results for moisture uptake for spray dried extracts of *Echinacea purpurea* prepared using a 10:1 alcohol to root ratio. FIG. 7 illustrates the results for moisture uptake for spray dried extracts of *Echinacea angustifolia* prepared using a 10:1 alcohol to root ratio.

TABLE 3

Moisture Uptake of *Echinacea purpurea* and *Echinacea angustifolia* extractions.

| Time in Minutes | 0 min. | 60 min. | 90 min. | 150 min. | 270 min. | 390 min. |
| --- | --- | --- | --- | --- | --- | --- |
| E. purpurea 1:10, unheated | 0 | 3.29% | 5.65% | 7.01% | 8.44% | 9.28% |
| E. purpurea 1:10, heated | 0 | 2.6% | 5.04% | 6.15% | 8.2% | 9.14% |
| E. angustifolia 1:10, unheated | 0 | 3.35% | 5.29% | 6.62% | 8.62% | 9.73% |
| E. angustifolia 1:10, heated | 0 | 3.11% | 4.8% | 6.2% | 8.01% | 9.02% |
| E. purpurea 1:7, unheated | 0 | 2.73% | 5.68% | 6.44% | 8.55% | 9.55% |
| E. purpurea 1:7, heated | 0 | 4.06% | 5.1% | 5.26% | 6.15% | 6.7% |
| E. angustifolia 1:7, unheated | 0 | 3.3% | 5.47% | 6.34% | 7.61% | 8.28% |
| E. angustifolia 1:7, heated | 0 | 1.87% | 3.7% | 5.15% | 7.32% | 8.6% |

Moisture uptake is measured as the percent increase in weight of the spray-dried powder over time. As illustrated in Table 3, the spray-dried powder from the heated extractions

TABLE 1

Percent soluble solids from heated and unheated *Echinacea purpurea* extractions using a 10:1 alcohol to root ratio

| | 15 min. | 30 min. | 60 min. | 90 min. | 105 min. | 120 min. | 150 min. |
| --- | --- | --- | --- | --- | --- | --- | --- |
| Unheated | 0.37% | 0.73% | 0.89% | 1.10% | 1.45% | 1.29% | 1.28% |
| Heated | 0.70% | 0.85% | 1.35% | 1.90% | 1.86% | 1.86% | 1.75% |

TABLE 2

Percent soluble solids from heated and unheated *Echinacea angustifolia* extractions using a 10:1 alcohol to root ratio

| | 15 min. | 30 min. | 60 min. | 90 min. | 105 min. | 120 min. | 150 min. |
| --- | --- | --- | --- | --- | --- | --- | --- |
| Unheated | 0.80% | 0.95% | 1.12% | 1.20% | 1.78% | 1.70% | 1.65% |
| Heated | 1.14% | 2.35% | 2.60% | 2.40% | 2.49% | 2.34% | 2.30% | absorbs less moisture than that of the unheated extractions. For example, spray-dried powder extract of *Echinacea purpurea* root, prepared using a 10:1 alcohol to root ratio, showed moisture uptake of 3.29 percent after 60 minutes from the unheated extraction, but only 2.6 percent after 60 minutes from the heated extraction. The moisture uptake data at 60 minutes is of particular interest because that is the approximate length of time during which the powder extract is exposed to air before tableting. The less moisture absorbed by the extract, the better the tableting characteristics of the powder.

In contrast, material extracted with unheated alcohol did not have any flow, was lumpy, and had a high moisture uptake. This material could not be tableted. (See Table 4, Column L). Material extracted with unheated alcohol had a very high ratio of raw material to dry extract. In other words, with the unheated alcohol extraction, much more starting material was required to yield a given amount of dry extract product (See Table 4, Column K).

Alkylamides, which are used as a marker compounds, are generally present in commercially available Echinacea at a level of about 0.5% alkylamides for *Echinacea angustifolia*, and about 0.1% for *Echinacea purpurea*. Using the extraction methods of the present invention, *Echinacea angustifolia* extracts have a level of alkylamides between 0.5% to 2.4%, with an average of 0.95%, and *Echinacea purpurea* extracts have a level of alkylamides between 0.136% to 0.534%, with an average of 0.25%. The extraction methods of the present invention, therefore yield a higher level of desired marker compounds.

The following examples describe extractions of *Echinacea purpurea* and *Echinacea angustifolia* according to the methods of the present invention. The results from these examples is summarized in Table 4.

EXAMPLE 1

*Echinacea purpurea* root

Alcohol to root ratio: 10:1

Temperature: unheated (ambient)

(Table 4, line 1).

Batches of 50 kg of root (tea cut) were used. The alcohol to root ratio was 10:1, and the concentration of the alcohol used was 70% (70% EtOH and 30% water). The alcohol was unheated. The 50 kgs of root were introduced into the tank through the manhole. Once the raw material was batched into the tank with 70% EtOH/30% $H_2O$, a 2-hour extraction was started. Samples were taken at 15-minute intervals to check soluble solids level.

Mass Balance: 50 kgs + 391 kgs ethanol (200 proof) + 150 kgs $H_2O$ = 493.5 kgs of liquid extract + 97.5 kgs Cake
(1.29% solids)   (60% to 65% moisture)

The solids were separated from the liquid in a decanter centrifuge and the liquid screened with an 80-mesh screen. Liquid extract was concentrated in an evaporator to obtain 29.60 kgs at 21.50% solids. The concentrate was checked for solids. Maltodextrin (M510) was then added in an amount equal to 50% of the solids level in the concentrate. For example, 29.60 kg concentrate×21.50% solids=6.36 kg solids. 6.36 kg solids×50%=3.18 kg maltodextrin added. (See Table 4, line 1) The pH was 4.7. The concentrate was spray dried in a spray dryer to yield only 56.04% powder. ([5.35 kg after spray drying/(6.36 kg total solids+3.18 kg carrier)]× 100=56%). The powder was very sticky, did not flow at all, and yielded only 5.35 kgs. The ratio of root to spray dried powder was 9.35:1.

EXAMPLE 2

*Echinacea purpurea* root

Alcohol to root ratio: 10:1

Temperature: heated (60° C./140° F.)

(See Table 4, line 2).

Batches of 50 kg of root (tea cut) were used. The alcohol to root ratio was 10: 1, and the concentration of the alcohol used was 70% (70% EtOH and 30% water). The alcohol was heated to 60° C. before the 50 kgs of root were introduced. The 50 kgs of root were introduced into the tank through the manhole. Once the raw material was batched into the tank with 70% EtOH/30% $H_2O$, a 2-hour extraction was started after reaching the desired temperature of 60° C. Samples were taken at 15-minute intervals to check soluble solids level.

Mass Balance: 50 kgs + 391 kgs ethanol (200 proof) + 150 kgs $H_2O$ = 518.2 kgs extract + 73.1 kgs Cake
(1.86% solids)   (58% to 60% moisture)

The solids were separated from the liquid in a decanter centrifuge and the liquid screened through an 80-mesh screen. Liquid extract was concentrated in an evaporator to obtain 42 kgs at 23% solids. The concentrate was checked for solids, and maltodextrin (M510) was added in an amount equal to 50% of the solids level in the concentrate. The pH was 5.1. The concentrate was spray dried to yield 76.05%.

EXAMPLE 3

*Echinacea angustifolia* root

Alcohol to root ratio: 10:1

Temperature: unheated (ambient)

(See Table 4, line 3)

Batches of 50 kg of root (tea cut) were used. The alcohol to root ratio was 10:1, and the concentration of the alcohol used was 70% (70% EtOH and 30% water). The alcohol was unheated. The 50 kgs of root were introduced into the tank through the manhole. Once the raw material was batched into the tank with 70% EtOH/30% $H_2O$, a 2-hour extraction was started. Samples were taken at 15-minute intervals to check soluble solids level.

Mass Balance: 50 kgs + 391 kgs Ethanol (200 proof) + 150 Kgs Water = 492.9 kgs of Extract + 98.1 kgs of Cake
(1.78% soluble solids)   (63 to 65% moisture)

The solids were separated from the liquid in a decanter centrifuge and the liquid screened through an 80-mesh screen. Liquid extract was concentrated in an evaporator to obtain 49 kgs at 18% solids. The concentrate was checked for solids, and maltodextrin (M510) was added in an amount equal to 50% of the solids level in the concentrate. The pH was 4.7. The concentrate was spray dried to yield 81.03%.

EXAMPLE 4

*Echinacea angustifolia* root

Alcohol to root ratio: 10:1

Temperature: heated (60° C./140° F.)

(See Table 4, line 4)

Batches of 50 kg of root (tea cut) were used. The alcohol to root ratio was 10: 1, and the concentration of the alcohol used was 70% (70% EtOH and 30% water). The alcohol was heated to 60° C. before the 50 kgs of root were introduced. The 50 kgs of root were introduced into the tank through the manhole. Once the raw material was batched into the tank with 70% EtOH/30% $H_2O$, a 2-hour extraction was started after reaching the desired temperature of 60° C. Samples were taken at 15-minute intervals to check soluble solids level.

| Mass Balance: | 50 kgs + 391 kgs Ethanol (200 proof) + 150 Kgs Water = 520.8 kgs of Extract + 70.2 kgs of Cake (2.40% soluble solids) (56 to 60% moisture) |
|---|---|

The solids were separated from the liquid in a decanter centrifuge and the liquid was screened through an 80-mesh screen. Liquid extract was concentrated in an evaporator to obtain 48.5 kgs at 26% solids. The concentrate was checked for solids, and maltodextrin (M510) was added in an amount equal to 50% of the solids level in the concentrate. The pH was 5.1. The concentrate was spray dried to yield 89.00%.

EXAMPLE 5

*Echinacea purpurea* root

Alcohol to root ratio: 7:1

Temperature: unheated (ambient)

(See Table 4, line 5)

Batches of 50 kg of root (tea cut) were used. The alcohol to root ratio was 7:1, and the concentration of the alcohol used was 70% (70% EtOH and 30% water). The alcohol was unheated. The 50 kgs of root were introduced into the tank through the manhole. Once the raw material was batched into the tank with 70% EtOH/30% $H_2O$, a 2-hour extraction was started. Samples were taken at 15- minute intervals to check soluble solids level.

| Mass Balance: | 50 kgs + 391 kgs Ethanol (200 proof) + 150 Kgs Water = 493.0 kgs of Extract + 98.0 kgs of Cake (1.21% soluble solids) (60 to 65% moisture) |
|---|---|

The solids were separated from the liquid in a decanter centrifuge, and the liquid was screened through an 80-mesh screen. Liquid extract was concentrated in an evaporator to obtain 26.0 kgs at 23% solids. The concentrate was checked for solids, and maltodextrin (M510) was added in an amount equal to 50% of the solids level in the concentrate. The pH was 4.7. The concentrate was spray dried to yield 66.50%.

EXAMPLE 6

*Echinacea purpurea* root

Alcohol to root ratio: 7:1

Temperature: heated (60° C./140° F.)

(See Table 4, line 6)

Batches of 50 kg of root (tea cut) were used. The alcohol to root ratio was 7:1, and the concentration of the alcohol used was 70% (70% EtOH and 30% water), The alcohol was heated to 60° C. before the 50 kgs of root were introduced. The 50 kgs of root were introduced into the tank through the manhole. Once the raw material was batched into the tank with 70% EtOH/30% $H_2O$, a 2-hour extraction was started after reaching the desired temperature of 60° C. Samples were taken at 15-minute intervals to check soluble solids level.

| Mass Balance: | 50 kgs + 391 kgs Ethanol (200 proof) + 150 Kgs Water = 509.0 kgs of Extract + 82.0 kgs of Cake (1.25% soluble solids) (58 to 60% moisture) |
|---|---|

The solids were separated from the liquid in a decanter centrifuge and the liquid was screened through an 80-mesh screen. Liquid extract was concentrated in an evaporator to obtain 27.76 kgs at 23% solids. The concentrate was checked for solids, and maltodextrin (M510) was added in an amount equal to 50% of the solids level in the concentrate. The pH was 5.1. The concentrate was spray dried to yield 84.44%.

EXAMPLE 7

*Echinacea angustifolia* root

Alcohol to root ratio: 7:1

Temperature: unheated (ambient)

(See Table 4, line 7)

Batches of 50 kg of root (tea cut) were used. The alcohol to root ratio was 7:1, and the concentration of the alcohol used was 70% (70% EtOH and 30% water). The alcohol was unheated. The 50 kgs of root were introduced into the tank through the manhole. Once the raw material was batched into the tank with 70% EtOH/30% $H_2O$, a 2-hour extraction was started. Samples were taken at 15-minute intervals to check soluble solids level.

| Mass Balance: | 50 kgs + 391 kgs Ethanol (200 proof) + 150 Kgs Water = 489.0 kgs of Extract + 102.0 kgs of Cake (1.076% soluble solids) (64 to 66% moisture) |
|---|---|

The solids were separated from the liquid in a decanter centrifuge, and the liquid was screened through an 80-mesh screen. Liquid extract was concentrated in an evaporator to obtain 22.80 kgs at 23% solids. The concentrate was checked for solids, and maltodextrin (M510) was added in an amount equal to 50% of the solids level in the concentrate. The pH was 4.7. The concentrate was spray dried to yield 51.05%. The material was of poor quality. It was light and fluffy, and also stuck to the spray dryer.

EXAMPLE 8

*Echinacea angustifolia* root

Alcohol to root ratio: 7:1

Temperature: heated (60° C./140° F.)

(See Table 4, line 8)

Batches of 50 kg of root (tea cut) were used. The alcohol to root ratio was 7:1, and the concentration of the alcohol used was 70% (70% EtOH and 30% water). The alcohol was heated to 60° C. before the 50 kgs of root were introduced. The 50 kgs of root were introduced into the tank through the manhole. Once the raw material was batched into the tank with 70% EtOH/30% $H_2O$, a 2-hour extraction was started after reaching the desired temperature of 60° C. Samples were taken at 15-minute intervals to check soluble solids level.

Mass Balance: 50 kgs + 391 kgs Ethanol (200 proof) + 150 Kgs Water = 519.0 kgs of Extract + 72.0 kgs of Cake
(2.3% soluble solids) (58 to 60% moisture)

The solids were separated from the liquid in a decanter centrifuge, and the liquid was screened through an 80-mesh screen. Liquid extract was concentrated in an evaporator to obtain 53.00 kgs at 22.5% solids. The concentrate was checked for solids, and maltodextrin (M510) was added in an amount equal to 50% of the solids level in the concentrate. The pH was 5.1. The concentrate was spray dried to yield 87.77%.

The results from Examples 1–8 are shown in Table 4 in lines 1–8, respectively.

words, the "Kgs Solids in Concentrate" for each unheated extraction divided by itself equals one (1). The "Solids Ratio Heated/Unheated" for the heated extraction is calculated by dividing the "Kgs Solids in Concentrate" for the heated extraction by the "Kgs Solids in Concentrate" for the unheated extraction in the same pair to produce a ratio. For example, in row 2, (9.66 Kgs Solids in Concentrate (Heated Extract Example 2))/(6.36 Kgs Solids in Concentrate (Unheated Extract Example 1))=1.52.

Column H, labeled "Kgs Carrier," indicates the mass of the carrier, in this case, Maltodextrin, that is added to the extract prior to spray drying. Maltodextrin (M510) is added in an amount equal to 50% of the solids level in the concentrate. The amount of carrier added is calculated by dividing the "Kgs Solids in Concentrate" from Column F by two (2). For example, in row 1, the "Kgs Solids in Concentrate" from Column F is 6.36 Kgs. (6.36 Kgs Solids in

TABLE 4

| Example Number | A Herb | B Alcohol to Root Ratio | C Extraction Temperature | D Kgs after Concentration | E % Solids in Concentrate | F Kgs Solids in Concentrate | G Solids Ratio Heated/ Unheated | H Kgs of Carrier | I Kgs after Spray drying | J % Yield | K Kgs Herb for 1 Kg Powder |
|---|---|---|---|---|---|---|---|---|---|---|---|
| 1 | E. purpurea | 10:1 | Ambient | 29.60 | 21.50 | 6.36 | 1.00 | 3.18 | 5.35 | 56.1% | 9.35 |
| 2 | E. purpurea | 10:1 | 60 C./140 F. | 42.00 | 23.00 | 9.66 | 1.52 | 4.83 | 11.02 | 76.0% | 4.54 |
| 3 | E. augustifolia | 10:1 | Ambient | 49.00 | 18.00 | 8.82 | 1.00 | 4.41 | 10.72 | 81.0% | 4.66 |
| 4 | E. augustifolia | 10:1 | 60 C./140 F. | 48.50 | 26.00 | 12.61 | 1.43 | 6.31 | 16.83 | 89.0% | 2.97 |
| 5 | E. purpurea | 7:1 | Ambient | 26.00 | 23.00 | 5.98 | 1.00 | 2.99 | 5.965 | 66.5% | 8.38 |
| 6 | E. purpurea | 7:1 | 60 C./140 F. | 27.76 | 23.00 | 6.38 | 1.07 | 3.19 | 8.087 | 84.4% | 6.18 |
| 7 | E. augustifolia | 7:1 | Ambient | 22.88 | 23.00 | 5.26 | 1.00 | 2.63 | 4.03 | 51.1% | 12.41 |
| 8 | E. augustifolia | 7:1 | 60 C./140 F. | 53.00 | 22.50 | 11.93 | 2.27 | 5.96 | 15.70 | 87.8% | 3.18 |

Table 4 is shows yields for the various Echinacea extractions described in examples 1–8.

The Column labeled "Example Number" numbers the rows in the table to correspond with the example numbers in the specification. For example, row 1 corresponds to Example 1. Column A, labeled "Herb," indicates which herb was used in the extraction, *Echinacea purpurea* or *Echinacea angustifolia*.

Column B, labeled "Alcohol to Root Ratio," indicates the alcohol to ratio use in the extraction, either 10:1 or 7:1.

Column C, labeled "Extraction Temperature," indicates the temperature at which the extraction was carried out, either ambient temperature or 60C./140F.

Column D, labeled "Kgs after Concentration," indicates the total mass of the concentrated liquid extract.

Column E, labeled "% Solids in Concentrate," indicates the percentage of soluble solids present in the concentrated liquid extract. The percentage of soluble solids is determined by measuring the refractive index of the concentrated liquid extract.

Column F, labeled "Kgs Solids in Concentrate," indicates the mass of soluble solids in the concentrated liquid extract. The mass of the soluble solids is calculated by multiplying the "Kgs after Concentration" from Column D by the "% Solids in Concentrate" from Column E, and dividing by 100. For example, in row 1, (29.60 Kgs of extract)(21.50% solids)/100=6.36 Kgs solids.

Column G, labeled "Solids Ratio Heated/Unheated," indicates the ratio of "Kgs Solids in Concentrate" from Column F for each pair of examples (pairs are 1 and 2; 3 and 4; 5 and 6; 7 and 8) comparing the heated extraction to the unheated extraction. In each case, the "Kgs Solids in Concentrate" for the unheated or ambient extraction is set at one (1). In other Concentrate)/2=3.18 Kgs. In this example, Maltodextrin is added in an amount equal to half of the level of solids, or 3.18 Kgs Maltodextrin is added.

Column I, labeled "Kgs after Spray Drying," indicates the yielded mass in Kgs of the solids after spray drying. The mass after spray drying includes the mass of the soluble solids and the mass of carrier added before spray drying.

Column J, labeled "% Yield," indicates the percentage of soluble solids yielded relative to the total mass of solids after spray drying. The "% Yield" is calculated by dividing the "Kgs after Spray Drying" from Column I by the sum of "Kgs Solids in Concentrate" from Column F and "Kgs Carrier" from Column H. The result is then multiplied by 100 to give a percentage. For example, in row 1, [(5.35 Kgs after spray drying)/(6.36 Kgs solids in concentrate)+(3.18 Kgs carrier)]×100=56.1%.

Column K, labeled "Kgs Herb for 1 Kg Powder," indicates the mass of the raw herb starting material required to yield 1 Kg of the extract powder. "Kgs Herb for 1 Kg Powder" is calculated by dividing the mass of the raw starting material, by the "Kgs after Spray Drying" from Column I. The mass of the raw starting material is 50 Kgs for each of the examples, 1–8. For example, in row 1, (50 Kgs starting material)/(5.35 Kgs after spray drying)=9.34 Kg root to make 1 Kg extract.

As illustrated by comparing the pairs of numbers in Column G, for each pair of extractions, the heated alcohol extraction yielded more soluble solids than the unheated extraction. As shown in Column J, the percent yield was also higher for each heated extract compared to its unheated pair. Consequently, as illustrated in Column K, for each pair, significantly less raw herb root is required to produce a given amount of spray dried extract for the heated extractions compared to the unheated extractions.

The experiments above show that by using a heated alcohol extraction process with a 10:1 alcohol to root ratio according to the present invention, the extraction yields up to 50% more soluble solids and high levels of nutrients or marker compounds than conventional extraction methods.

By using the methods of the present invention, there is a greater yield of powder when the alcohol/water solvent mixture is evaporated off the liquid extract. A greater yield from a given amount of starting material means that the process is economically more efficient than traditional ambient temperature alcohol/water extractions. In both cases, using *Echinacea purpurea* and *Echinacea angustifolia*, the product not only was produced more efficiently and at a lower cost, but also with a higher level of the marker compounds, alkylamides.

In summary, there are numerous advantages to using the extraction methods of the present invention. These extraction methods produced 40% to 25 50% more soluble solids, concentrated well, and spray dried (with M510-Maltodextrin) at a higher efficiency to produce a better (non-sticking, low moisture uptake) spray dried powder.

Although the description above contains many specifics, these should not be construed as limiting the scope of the invention, but as merely providing illustrations of some of the presently preferred embodiments of this invention. Thus the scope of this invention should be determined by the appended claims and their legal equivalents, rather than by the examples given.

What is claimed:

1. A method of producing a plant extract comprising:
   a) providing Echinacea plant material;
   b) contacting the Echinacea plant material with an alcohol solution to form a mixture, the alcohol solution comprising about 70% alcohol and about 30% water by weight, and being used in an amount sufficient to yield a ratio of about 1:10 by weight of Echinacea plant material to alcohol;
   c) heating the mixture to between about 60° C. and about 70° C.;
   d) maintaining the temperature of the mixture for at least about 2 hours, thereby yielding a liquid extract and non-soluble solids; and
   e) wherein the liquid extract has an alkylamide level of about 0.1% to about 2.4% by weight.

2. The method of claim 1 further comprising:
   a) separating the non-soluble solids from the liquid extract;
   b) distilling at least a portion of the alcohol off of the liquid extract by raising the temperature of the liquid extract to a temperature above the boiling point of the alcohol.

3. The method of claim 1 further comprising agitating the mixture in step d.

4. The method of claim 1 wherein the alcohol is ethanol.

5. The method of claim 2 further comprising filtering the liquid extract.

6. The method of claim 5, wherein the filter has a mesh of about 200 mesh or greater.

7. A plant extract produced by a High temperature extraction process, comprising the following steps:
   a) providing Echinacea plant material;
   b) contacting the Echinacea plant material with an alcohol solution to form a mixture, the alcohol solution comprising about 70% alcohol and about 30% water by weight, and being used in an amount sufficient to yield a ratio of about 1:10 by weight of Echinacea plant material to alcohol;
   c) heating the mixture to about 60° C.;
   d) maintaining the temperature of the mixture at about 60° C. for at least about 2 hours, thereby yielding a liquid extract and non-soluble solids; and
   e) wherein the liquid extract has an alkylamide level of about 0.95% by weight or greater.

8. A method of producing a plant extract comprising:
   a) providing Echinacea plant material;
   b) contacting the Echinacea plant material with an alcohol solution to form a mixture, the alcohol solution being used in an amount sufficient to yield a predetermined ratio of Echinacea plant material to alcohol;
   c) heating the mixture to between about 50° C. and about 65° C.;
   d) maintaining the temperature of the mixture for between about 90 and about 120 minutes, thereby yielding a liquid extract and non-soluble solids; and
   e) wherein the liquid extract has an alkylamide level of about 0.1% to about 2.4% by weight.

9. The method of claim 8 wherein the alcohol solution is between about 50% to about 90% ethanol.

10. The method of claim 8 wherein the alcohol solution is between about 60% to about 80% ethanol.

11. The method of claim 8 wherein the alcohol solution is between about 65% to about 75% ethanol.

12. The method of claim 8 wherein the alcohol solution is 70% ethanol.

13. The method of claim 8 wherein the ratio of plant material to alcohol is between about 1:7 and about 1:10 by weight.

14. The method of claim 8 wherein the ratio of plant material to alcohol is about 1:10 by weight.

15. The method of claim 1 further comprising:
   a) separating the non-soluble solids from the liquid extract;
   b) distilling at least a portion of the alcohol off of the non-soluble solids and recovering the distilled alcohol.

16. A method of producing a tablet that contains a plant extract comprising:
   a) providing Echinacea plant material;
   b) contacting the Echinacea plant material with an alcohol solution to form a mixture, the alcohol solution comprising about 70% alcohol and about 30% water by weight, and being used in an amount sufficient to yield a ratio of about 1:10 by weight of Echinacea plant material to alcohol;
   c) heating the mixture to between about 50° C. and about 65° C.;
   d) maintaining the temperature of the mixture for between about 90 and about 120 minutes, thereby yielding a liquid extract and non-soluble solids;
   e) separating the non-soluble solids from the liquid extract;
   f) drying the liquid extract to form a powder extract;
   g) directly compressing the powder extract with other excipients to form a tablet.

17. A method of producing a plant extract comprising:
   a) providing Echinacea plant material;
   b) contacting the Echinacea plant material with an alcohol solution to form a mixture, the alcohol solution comprising about 70% alcohol and about 30% water by weight, and being used in an amount sufficient to yield a ratio of about 1:10 by weight of Echinacea plant material to alcohol;

c) heating the mixture to between about 50° C. and about 70° C.;

d) maintaining the temperature of the mixture for at least about 90 minutes, thereby yielding a liquid extract and non-soluble solids; and e) wherein the liquid extract has an alkylamide level of at least about 0.1% by weight.

18. The method of claim 17 wherein the liquid extract has an alkylamide level of at least about 0.136% by weight.

19. The method of claim 17 wherein the liquid extract has an alkylamide level of at least about 0.25% by weight.

20. The method of claim 17 wherein the liquid extract has an alkylamide level of at least about 0.534% by weight.

* * * * *